US010907129B2

(12) United States Patent
Opel et al.

(10) Patent No.: US 10,907,129 B2
(45) Date of Patent: Feb. 2, 2021

(54) APPARATUS FOR PROCESSING SAMPLES CONTAINING BIOLOGICAL CELLS

(71) Applicant: ALS Automated Lab Solutions GmbH, Jena (DE)

(72) Inventors: Matthias Opel, Jena (DE); David Unglaub, Neustadt/Orla (DE); Jens Eberhardt, Gera (DE); Gerd Bornmann, Weimar (DE)

(73) Assignee: ALS Automated Lab Solutions GmbH, Jena (DE)

( * ) Notice: Subject to any disclaimer, the term of this patent is extended or adjusted under 35 U.S.C. 154(b) by 0 days.

(21) Appl. No.: 16/396,762

(22) Filed: Apr. 28, 2019

(65) Prior Publication Data

US 2019/0249133 A1 Aug. 15, 2019

Related U.S. Application Data (63) Continuation of application No. PCT/DE2017/100923, filed on Oct. 28, 2017.

(30) Foreign Application Priority Data

Oct. 28, 2016 (DE) .................. 10 2016 120 726

(51) Int. Cl.
*C12M 1/33* (2006.01)
*C12M 1/00* (2006.01)
(Continued)

(52) U.S. Cl.
CPC ............ *C12M 45/02* (2013.01); *C12M 29/06* (2013.01); *C12M 33/04* (2013.01); *C12M 37/02* (2013.01);
(Continued)

(58) Field of Classification Search
CPC ......... A61J 1/20; A61J 3/002; B01F 11/0008; B01F 11/0017; B01F 13/1055; B01F 13/1063; B01F 15/00253; B01F 5/0453; B01F 5/046; B65B 31/02; B65B 31/024; B65B 3/003; B65B 55/16; B65B 59/00; B65B 1/30; B65B 57/20; G07F 11/002; G07F 11/165; G07F 11/70; B07C 1/20; B07C 3/00; B07C 3/02; B07C 5/00; B07C 5/36; B65G 15/00; B65G 15/06; B65G 33/02; B65G 47/46; B65G 47/52; G06K 9/00369; G06Q 50/28; G06Q 10/06; G06Q 30/0607; G06Q 50/02; H04N 21/4318; H04N 21/44008; H04N 21/44222; H04N 21/4668; H04N 21/475; H04N 7/163; Y10S 209/90; Y10S 435/973; Y10S 436/805; A01F 11/00; A01F 12/50; B01L 2300/044; B01L 2300/047; B01L 2300/049; B01L 2300/0681; B01L 2300/0829; B01L 2400/0409; B01L 2400/065; B01L 2400/0683; B01L 3/502; B01L 3/5021; B01L 3/5025; B01L 3/50255; B04B 2005/0435; B04B 5/0407; B04B 5/0421; B04B 7/08; C12M 29/06; C12M 33/04; C12M 37/02; C12M 41/14; C12M 41/18; C12M 45/02; C12M 45/06; C12M 45/20; A01B 79/005; A01C 21/005; A01G 9/247; G01N 15/14; G01N 15/1404; G01N 15/1459; G01N 1/14; G01N 2015/0069;
(Continued)

(56) References Cited

U.S. PATENT DOCUMENTS 5,891,734 A * 4/1999 Gill .................. B01F 5/0453
422/63
6,122,396 A 9/2000 King et al.
(Continued)

FOREIGN PATENT DOCUMENTS

CN 202297580 U 7/2012
EP 633207 A1 1/1995
(Continued)

OTHER PUBLICATIONS

International Search Report of the European Patent Office in PCT/DE2017/100923 (from which this application claims priority) dated Feb. 2, 2018 and English-language translation thereof.
(Continued)

*Primary Examiner* — Deborah K Ware
(74) *Attorney, Agent, or Firm* — Falk Ewers; Ewers IP Law PLLC (57) ABSTRACT

An apparatus and a method for the automated processing of samples containing biological cells—in particular, of blood samples or other cell samples is provided. The apparatus has a sample receiving device configured to receive samples, an auxiliary material receiving device configured to receive auxiliary materials, a sample carrier receiving device configured to receive sample carriers, a discharge device configured to discharge samples from a discharge position, and a capture device configured to capture discharged samples in a capture position to obtain prepared samples, and at least one temperature control device for controlling the temperature of at least one of the sample carriers. The distance between the discharge position and the capture position can be adjusted to a prespecified height. The method includes wetting a temperature-controlled sample carrier with at least one auxiliary material and discharging the sample onto the wetted temperature-controlled sample carrier from a prespecified height.

10 Claims, 4 Drawing Sheets

(51) Int. Cl.
*C12M 1/26* (2006.01)
*C12M 1/12* (2006.01)
*C12M 1/02* (2006.01)

(52) U.S. Cl.
CPC ............ *C12M 41/14* (2013.01); *C12M 41/18* (2013.01); *C12M 45/06* (2013.01); *C12M 45/20* (2013.01)

(58) Field of Classification Search
CPC ... G01N 2015/0076; G01N 2015/0084; G01N 2015/1413; G01N 2035/00356; G01N 2035/00524; G01N 2035/1032; G01N 35/0092; G01N 35/10; G01N 35/1004; G01N 35/109; G01N 35/1095; Y10T 436/11; Y10T 436/25; Y10T 436/25125; Y10T 436/2575
See application file for complete search history.

(56) References Cited

U.S. PATENT DOCUMENTS

| | | | | |
|---|---|---|---|---|
| 6,850,252 | B1* | 2/2005 | Hoffberg | G06K 9/00369 348/E7.061 |
| 7,783,383 | B2* | 8/2010 | Eliuk | A61J 1/20 141/1 |
| 7,813,822 | B1* | 10/2010 | Hoffberg | G06K 9/00369 381/73.1 |
| 7,930,066 | B2* | 4/2011 | Eliuk | A61J 1/20 700/245 |
| 7,974,714 | B2* | 7/2011 | Hoffberg | G06K 9/00369 360/75 |
| 8,457,781 | B2* | 6/2013 | Bailey | B07C 3/00 700/224 |
| 8,943,785 | B2* | 2/2015 | Blickhan | G06Q 10/06 53/500 |
| 9,020,634 | B2* | 4/2015 | Bailey | B07C 3/00 700/224 |
| 9,043,019 | B2* | 5/2015 | Eliuk | A61J 1/20 221/191 |
| 9,457,359 | B2* | 10/2016 | Von Stetten | B01L 3/502 |
| 9,579,255 | B2* | 2/2017 | Eliuk | A61J 1/20 |
| 2003/0103662 | A1 | 6/2003 | Finkbeiner | |
| 2007/0053513 | A1* | 3/2007 | Hoffberg | G06K 9/00369 380/201 |
| 2010/0198392 | A1* | 8/2010 | Eliuk | A61J 1/20 700/216 |
| 2011/0046775 | A1* | 2/2011 | Bailey | B07C 3/00 700/224 |
| 2011/0047042 | A1* | 2/2011 | Blickhan | G06Q 10/06 705/26.25 |
| 2011/0208350 | A1* | 8/2011 | Eliuk | A61J 1/20 700/240 |
| 2013/0252796 | A1* | 9/2013 | Von Stetten | B01L 3/502 494/8 |
| 2014/0148944 | A1* | 5/2014 | Bailey | B07C 3/00 700/224 |
| 2015/0250678 | A1* | 9/2015 | Eliuk | A61J 1/20 700/239 |
| 2019/0249133 | A1* | 8/2019 | Opel | C12M 45/02 |
| 2019/0259108 | A1* | 8/2019 | Bongartz | A01B 79/005 |

FOREIGN PATENT DOCUMENTS

| | | |
|---|---|---|
| EP | 1502649 A1 | 2/2005 |
| WO | 0013609 A2 | 3/2000 |
| WO | 03008934 A1 | 1/2003 |

OTHER PUBLICATIONS

International Preliminary Report on Patentability of the European Patent Office in PCT/DE2017/100923 (from which his application claims priority) dated Apr. 30, 2019 and English-language translation thereof.

* cited by examiner

APPARATUS FOR PROCESSING SAMPLES CONTAINING BIOLOGICAL CELLS

CROSS REFERENCE TO RELATED APPLICATIONS

This application is a continuation application of international patent application PCT/DE2017/100923, filed Oct. 28, 2017, designating the United States and claiming priority to German application 10 2016 120 726.8, filed Oct. 28, 2016, and the entire content of both applications is incorporated herein by reference.

TECHNICAL FIELD

The disclosure relates to an apparatus and a method for processing samples containing biological cells—in particular, blood samples or cell samples.

BACKGROUND

The importance of genetic and/or molecular biological analyses is growing in the life sciences and the medical field. Particularly in the areas of prognosis, diagnosis, and documentation of, for example, genetic defects or tumor diseases, methods for preparing cell samples, with the aim of making cell components analytically accessible, have become indispensable.

Part of this analysis is based on the destruction of the cell membrane by dropping a preprocessed cell sample on a sample carrier. This breaks the cell membrane, and emerging cell components—including chromosomes—are available for subsequent procedures such as staining, and for analysis steps such as an image analysis, for example. The manual preparation of a cell sample for analysis of components of the cell sample usually includes the following steps:

(i) Sample preparation: The cell sample with cells containing cell components to be subjected to analysis is usually available in the form of raw sample material. First, it is necessary to obtain the cell sample from the raw sample material. Depending on the cell type, this step can require different procedures. However, it generally consists of enriching and purifying the raw sample material by, for example, centrifuging and optionally further steps such as culturing the cells to generate the cell sample which will be analyzed. For example, it is necessary when creating a chromosome preparation to stimulate cell division and to interrupt the process during nuclear division.

(ii) Sample processing: The cells of the cell sample obtained in step (i) are processed to allow the cell membrane to break apart later. By way of example, by suitable methods, the cell envelopes—that is, depending on the type of cell, the cell wall, the cell membrane or the nuclear membrane, for example—are removed. Depending on the cell constituents which will be analyzed, the cell sample may be fixed. By adding suitable buffers—for example, methanol and acetic acid—the properties of the cell membrane are changed so that it breaks or bursts when a force is applied. A buffer or mixture of several buffers can be used. The type of buffer used depends on the type of sample and the analysis to which the components of the prepared cell sample will be subjected.

(iii) Optional density adjustment: In some cases, it can be desirable to adjust the cell density in the cell sample.

(iv) Sample carrier preparation: The sample carrier is usually wetted with a buffer solution in order to positively influence the distribution of the emerging cell constituents. The sample carrier is usually a slide for a microscope.

(v) Dropwise deposition: The cell sample is dropped in individual drops from a defined height onto the sample carrier which is inclined with respect to the direction in which the drops fall.

(vi) Propagation: Cell constituents emerging from the cell upon impact of the cell sample should run on the wetted, inclined slide. The aim is to obtain an optimal distribution—in particular, separation—of the cell constituents. This requires a waiting time.

(vii) Optional drying and immobilization: It is expedient in some cases to dry the cell sample on the sample carrier. The buffer evaporates during this process. In this way, the cell sample, including the released cell components, can be immobilized for subsequent analysis.

Following such manual preparation, the cell sample obtained in step (vi) or step (vii) can be subjected to analysis. Depending on the analytical method and the analysis objective, further staining steps or reactive solutions may be used before analysis of the cell sample—for example, by microscopic examination.

However, it has been found that the result and quality of the analysis of the manually prepared cell sample are influenced by factors related to the execution of the cell sample preparation steps. The preparation of the cell sample is such a sensitive process that, in addition to the skills of the laboratory technician performing the preparation, environmental conditions which have an impact on the cell samples and on liquids consisting of one or more components also influence not only the preparation itself but also the analysis. Not least of all, due to the high volume of samples in the laboratory, it is often not possible to wait for the process environment to stabilize before starting the sample preparation. The multiple analysis of a sample in the same laboratory can therefore itself lead to qualitatively variable results.

SUMMARY

It is an object of the disclosure to eliminate the disadvantages of the prior art. In particular, it is an objective to provide an apparatus for processing samples containing biological cells which offers high stability, high reliability, and good reproducibility of the processed samples obtained using the apparatus. Furthermore, it is an object to provide a method by which samples containing biological cells can be processed.

The object is achieved by an apparatus and a method for automated processing of samples as described herein.

The disclosure provides an apparatus for automated processing of samples containing cells—in particular, of blood samples or other cell samples. The apparatus has at least the following components:
  a sample receiving device configured to receive one or more samples;
  an auxiliary material receiving device configured to receive one or more auxiliary materials;
  a sample carrier receiving device configured to receive one or more sample carriers;
  a discharge device configured to discharge one or more samples from a discharge position; and
  a capture device configured to capture one or more discharged samples in a capture position to obtain one or more prepared samples.

The distance between the discharge position and the capture position, which is also referred to below as the discharge height, is adjustable to a prespecified height. The apparatus furthermore has at least one temperature control device configured to control the temperature of at least one of the sample carriers. In this case, the temperature of one or more sample carriers can be directly controlled by a temperature control device, such as a heating and/or cooling element. Alternatively or additionally, the one or more sample carriers can be arranged in a temperature-controlled region of the apparatus. Typically, the sample carrier is cooled until the sample is applied to it. Then, the sample carrier can be heated. The temperature control device can have an actuator for setting a prespecified angle of inclination of the sample carrier.

For the temperature control of the sample carrier, there may be a single temperature control device which allows for a temperature control—that is to say, a cooling and heating—of the sample carrier in a single position. This is the single heating and cooling position. It can be a heating and cooling element such as a heating and cooling block. Alternatively, there can be two temperature control devices, wherein a first temperature control device is arranged in a first position—for example, for cooling the sample carrier before and during the discharge of the sample—and a second temperature control device is arranged in a second position—for example, for heating the sample carrier after the sample is discharged. This is the separate heating and cooling position. The first temperature control device can be a cooling element, such as a cooling block, and the second temperature control device can be a heating element, such as a heating block.

The apparatus according to an aspect of the disclosure can be an automated apparatus.

Several samples can be prepared simultaneously by the apparatus according to an aspect of the disclosure.

The discharge device can have a pipetting system with a pipetting head which is movable at least along one axis, typically two axes, and particularly typically in the x-, y-, and z-directions. Samples can be taken up with the pipetting system and discharged onto the sample carriers (i.e., with respect to the sample carrier: dropped onto the sample carrier). To provide for movement of the pipetting head, the discharge unit can have robotics. The robotics can be controlled by a control device. The discharge device can be a pipetting robot. The control device can be a data processing unit. The data processing unit is expediently arranged outside the housing, but can also be integrated into the housing or into the apparatus according to an aspect of the disclosure. It can communicate with the discharge device via a data connection—for example a cable. The pipetting head can carry dosing means such as pipettes, capillaries, or syringes. In particular, the dosing means enable taking up a prespecified amount of the sample from the sample containers. Alternatively or additionally, the discharge device can have at least one pipetting channel for removing a predefined amount of the sample from a sample container and for conveying the sample into the discharge position.

The pipetting system can also be used to mix the buffer from auxiliary materials. A separate mixing device, and a conveyor configured to convey one or more auxiliary materials to the mixing device, are therefore not required.

The pipetting system can be used for wetting the sample carrier with one or more auxiliary materials—for example, with a buffer. A separate wetting device and conveyor configured to convey one or more auxiliary materials to the wetting device are therefore not required. One or more auxiliary materials—for example, a buffer—can be dropped onto the sample carrier by the pipetting system.

It is even possible to adjust the sample concentration—which is explained below—via the pipetting system.

The pipette can have a replaceable tip or a replaceable needle. The needle can be a hollow needle. The needles can be washable. The apparatus according to an aspect of the disclosure can have a holding device for the pipette tips and/or needles, which is referred to below as a pipette tip holding device. The pipette tip holding device can be arranged in the apparatus, typically in its working area.

Samples, sample carriers and—if one or more auxiliary materials are used—the auxiliary material(s) can be cooled to a defined temperature below the ambient temperature—that is, the room temperature—before the sample is discharged onto the sample carrier. Thus, the lysis of the cells favors and increases the effectiveness of an auxiliary material, such as a buffer, and the qualitative deterioration of the samples and the buffer can be prevented.

The disclosure is intended for the processing of biological samples containing cells. The term "processing" can include the preparation of the samples for subsequent analysis or the preparation and analysis of the samples. The analysis in both cases can be, for example, a genetic investigation, a molecular biology investigation, or both.

In particular, the apparatus according to an aspect of the disclosure can have as an additional component an analysis device configured to analyze the discharged sample located on the sample carrier. In this case, the sample is not only processed, but also undergoes an analysis within the apparatus. The analysis device can be an imaging device—for example, a microscope with a camera—as well as an image-evaluating unit—for example, a personal computer with image processing software. The imaging device enables the acquisition of a high-quality image of the sample containing biological cells, the evaluation of which can be done manually or with image analysis by image processing software. The analysis can be directly connected to the sample preparation.

The cells that can be included in the sample are, for example, eukaryotic cells. The disclosure makes it possible to make cell components of the cells contained in the sample accessible, and for example, visible, for subsequent analysis. The sample can be, for example, a blood sample. The sample is also referred to below as a cell sample.

The distance between the discharge position and the capture position can be adjusted to a value between 0.1 and 800 mm. The distance between the discharge and the capture position is also referred to below as the discharge height. The inclination angle of the sample carrier can be adjusted to a value between 0 and 90° with respect to a horizontal plane. Inclination angles of 15 to 75° are typical. The collecting device can have a holder for receiving one of the sample carriers. The capture device can be guided in such a manner that the sample carrier in the holder reaches the capture position. The capture device can have an actuator for setting a prespecified angle of inclination of the sample carrier. Typically, the sample is discharged in the form of a drop. The flow of the drop of the sample is dependent on one or more of the factors: sample type, analysis objective, and impact velocity—although this list is not exhaustive.

The capture device can be positioned at a fixed location or be movable along at least one axis, typically two axes and particularly typically in the x-, y-, and z-directions. At least one of the axes should be a horizontal axis. The apparatus according to an aspect of the disclosure can have a handling unit which can remove one or more sample carriers from the sample carrier receiving device and transfer them to the capture device. Alternatively, the capture device can have a handling unit which is capable of removing a sample carrier from the sample carrier receiving device and guides the sample carrier into the capture position. The handling unit can provide for temperature control of the samples. The inclination of the sample carrier and/or the discharge height of the sample drop can be adjusted by the handling unit. Likewise, the handling unit can be used to dip the sample carrier in a buffer or to position the sample carrier in such a manner that buffer can be applied by the pipetting system.

In the apparatus, one or more protective elements can be arranged to realize a splash guard. Advantageously, the discharge path which the sample travels from the discharge position to the capture position is wholly or partially between such guard elements. The guard element can be, for example, a tube with the discharge path running through the interior thereof. Alternatively or additionally, partitions can also be attached as protective elements between the sample carriers, preventing contamination of the adjacent regions with sample sprays. These protective elements can be designed so that they can be washed and sterilized, or used as single-use, disposable products. For example, the protective elements can be made of plastic, paper, cardboard, etc.

The sample carriers can be slides, such as glass slides. The sample carrier is optionally in a cooled state during capture of the sample. It can either be actively cooled or positioned on a cold block, or covered with cold buffer. To cover the sample carrier with cold buffer, the sample carrier can be immersed, for example, in the buffer.

If this task is not performed by the pipetting system, the apparatus according to an aspect of the disclosure can have a wetting device configured to wet the sample carrier with one or more auxiliary materials.

One or more auxiliary materials can be temperature controlled by a temperature control device—for example, a cooling element. This is a direct temperature control. Alternatively or additionally, the auxiliary material(s) is/are arranged in a temperature-controlled area. The temperature-controlled area in which the sample carriers are arranged, and the temperature-controlled area in which the auxiliary material(s) is/are arranged can be the same temperature-controlled area. The temperature-controlled area can be the temperature-controlled storage area described below, which is constructed together with a working area in a housing. However, instead of being arranged in the temperature-controlled storage area, the auxiliary material(s) can be arranged in a temperature-controlled working area sub-region of the working area.

If coated sample carriers are used, wetting may not be necessary. In this case, there is no need for wetting, and therefore no need to furnish and control the temperature of auxiliary materials needed for wetting. The coated sample carrier can carry a coating that enables a temporary or permanent immobilization of components of the ruptured sample on the sample carrier. For example, the sample carrier can be coated with antibodies. In this way, for example, proteins from the ruptured sample can be immobilized on the sample carrier. In another exemplary embodiment, the sample carrier can be coated with proteins. In this way, for example, antibodies from the ruptured sample can be immobilized on the sample carrier.

The sample receiving device can be a rack. The sample receiving device can receive one or more samples. The samples can be introduced into the sample receiving device via the feed which is constructed in the housing. Alternatively, the sample receiving device can be introduced as such via the feed which is constructed in the housing. In this case, the sample or samples are introduced into the sample receiving device prior to the insertion of the sample receiving device into the housing. Conveniently, the samples are positioned in sample containers when they are inserted into the sample receiving device. In this case, the sample containers can either be inserted already opened, or can be automatically opened by an opening device of the apparatus according to an aspect of the disclosure.

The auxiliary material receiving device serves to receive one or more auxiliary materials. The apparatus according to an aspect of the disclosure can have a plurality of auxiliary material receiving devices. An auxiliary material is a buffer or a substance needed to make a buffer. Such substances are, for example, an alcohol solution such as a methanol solution, and an acid solution such as an acetic acid solution. Conveniently, the auxiliary materials are in auxiliary material containers when they are inserted into the auxiliary material receiving device. The auxiliary material containers can either be inserted already opened, or can be automatically opened by an opening device of the apparatus according to an aspect of the disclosure.

The apparatus according to an aspect of the disclosure can have, as a further component, a mixing device configured to produce a mixture of auxiliary materials. However, this is not necessary. The mixing device can be arranged in the housing. However, the mixing device can also be part of a wetting device or a pipetting channel. By way of example, the auxiliary material receiving device can be used to separately receive all substances that are required for the production of the buffer. These can be two or more substances. In one exemplary embodiment, the buffer is mixed with two substances—an alcohol and an acid. The substances required for the preparation of the buffer can be mixed in the mixing device to form a mixture. This mixture can then be used as a buffer. For the preparation of the mixture, any amount of the auxiliary material can be conveyed to the mixing device, as long as it is defined. The quantities of the auxiliary materials can be specified by the user. A mixing device is not required if prefabricated buffers are used.

If a wetting device is included, it serves for wetting the sample carrier with one or more auxiliary materials. In particular, the wetting device serves for wetting the sample carrier with a buffer. By way of example, the wetting device can have one or more nozzles with which one or more auxiliary materials, for example a buffer, are applied to the sample carrier. Alternatively, the wetting device can include a reservoir in which one or more auxiliary materials, for example a buffer, are located and into which the sample carrier can be immersed. The wetting of the sample carrier is part of the preprocessing of the same. One or more auxiliary materials can be mixed or sequentially applied to a sample carrier. In one exemplary embodiment, the auxiliary material is a buffer. In another exemplary embodiment, it is a combination of various auxiliary materials—which can be different buffers.

One or more conveyors can be included for conveying the auxiliary material(s) from the respective auxiliary material receiving device to the wetting device. Examples of a conveyor are a pump, a pump system, one or more washable needles, one or more pipettes. A pipette can have a replaceable tip.

The sample carrier receiving device can be a rack. The sample carrier receiving device can receive the unused sample carriers—that is, the sample carriers onto which a sample will be dropped—and the used sample carriers—that is, the sample carriers onto which a sample has already been dropped. The sample carrier receiving device can be temperature-controlled—typically cooled.

The apparatus according to an aspect of the disclosure can have a device configured to determine the cell density in the sample. This device is referred to below as cell density measuring device. The determination of the cell density in the sample can be used to set a prespecified density of cells in the sample before it is discharged. If the cell density is above a prespecified value, for example, a buffer or a buffer mixture can be added to the sample in order to set a defined cell density. One or more conveyors can be included to convey the auxiliary material(s) from the auxiliary material receiving device to the sample container in which the sample is located. These conveyors are also referred to as supply means. The cell density in the sample reflects the concentration of cells in the sample, which is why it is also referred to as cell density concentration or sample concentration. The measurement of the cell density can be used to set further process parameters. These include one or more of the following parameters: inclination angle, ambient conditions, temperature of the sample carriers, ambient temperature, and discharge height.

The apparatus according to an aspect of the disclosure can have a storage area in which at least the sample carrier receiving device is arranged. The storage area can be at the ambient temperature or can be temperature-controlled—typically cooled. The storage area is then a temperature-controlled area. If the apparatus according to an aspect of the disclosure has a temperature-controlled—typically cooled—storage area, it is also possible to arrange the auxiliary material receiving device next to the sample carrier receiving device in the temperature-controlled area. The apparatus according to an aspect of the disclosure can have a working area in which at least the discharge device and the capture device are arranged. The working area can be temperature-controlled—for example, cooled or heated. The working area can be regulated to a specific humidity. Typically, the sample receiving device is arranged in the working area.

If the storage area is not a temperature-controlled storage area, then the auxiliary material receiving device is typically arranged in the working area. For this purpose, a temperature-controlled working area sub-region can be provided in the working area. The temperature-controlled working area sub-region is typically a cooled area. One or more auxiliary material receiving devices can be arranged in the temperature-controlled working area sub-region. The auxiliary materials received by these auxiliary material receiving devices can be temperature-controlled—typically cooled. The sample receiving device can also be arranged in the working area sub-region.

The storage area and the working area can be provided in the housing. Conveniently, the working area adjoins the storage area.

In an exemplary embodiment, the apparatus according to an aspect of the disclosure includes a housing in which one or more components of the apparatus are arranged. At least one space can be provided in the housing, in which physical and/or chemical conditions can be set which are different from those of the environment. This particularly relates to one or more of the following conditions: temperature, pressure and composition of the gaseous phase. This gaseous phase is also referred to below as the working gas. The space can be the storage area, the working area sub-region, the entire working area, or the entire interior of the housing. The temperature and/or the humidity, typically both, in the region of the housing can differ from those of the environment. Typically, the temperature is below the ambient temperature. The ambient temperature is usually the room temperature. The temperature can be, at least in a temperature-controlled region in the housing, below 0° C.—for example, −20° C. The humidity can be adjusted depending on the sample type, the preprocessing and the ambient conditions. The working gas can be air. The apparatus according to an aspect of the disclosure can have a device for the preparation of the working gas, which generates a purified, homogeneous gas stream. The device for preparing the working gas can be a filter. The apparatus according to an aspect of the disclosure can further include a conveyor configured to convey the working gas to the device for preparing the working gas and away from the device for preparing the working gas. The conveyor configured to convey the working gas can be a fan. The physical and/or chemical conditions in the apparatus or in a region of the apparatus are also referred to below as the climate. Typically, at least one climate-controlled, sterile space is formed in the housing. This can be the working area, the storage area or both. A laminar flow of a working gas can be established in the housing.

In particular, the following components of the apparatus according to an aspect of the disclosure can be arranged in the housing: at least one auxiliary material receiving device, the sample carrier receiving device, the discharge device, and the capture device. The wetting device configured to wet the sample carrier with one or more auxiliary materials, if provided, can also be arranged in the housing. The analysis device can also be arranged in the housing. The apparatus according to an aspect of the disclosure can have a feed for introducing one or more samples into the housing. The sample receiving device can be arranged in the housing. The working area sub-region can be formed in the housing in such a manner that the samples can be introduced via the feed into the working area sub-region.

By the housing, an enclosure of the components of the system which come into contact with the sample can be achieved, as is particularly advantageous for clinical applications. The necessary sterility of the sample and process environment can be provided by an internal, homogenous, purified airflow into the housing. The apparatus according to an aspect of the disclosure can be connected to an exhaust system into which filtered exhaust air can be discharged from the interior of the housing. This can be expedient, or required by law, especially when potentially hazardous substances or combinations that form hazardous substances are used.

The apparatus according to an aspect of the disclosure can have at least one identification device (for example, a barcode reader) with which identifiers (for example, barcodes) which are positioned on the sample container, sample carrier and/or reagent container can be identified. The identification device (for example, a barcode reader) can also be used to identify consumables, such as pipette tips or their storage containers. This makes it easier to make assignments to samples and sample carriers, and allows process control—which is also referred to as tracking. The identifier (for example, a barcode) can be, for example, optical codes—in particular, a barcode—or RFID tags or other identifiers.

In accordance with an aspect of the disclosure, a method is also provided for automatic processing of samples containing biological cells—in particular blood samples or other cell samples. In the method, a temperature-controlled sample carrier is wetted with one or more temperature-controlled auxiliary materials, and a sample is discharged onto the wetted sample carrier from a prespecified height.

Typically, the temperature-controlled sample carrier and the temperature-controlled auxiliary material(s) are cooled to a temperature below the ambient temperature, more typically below 0° C., and particularly typically −20° C. Typically, the sample is cooled to a temperature below room temperature before it is discharged onto the temperature-controlled sample carrier.

The temperature-controlled sample carrier can be inclined to a prespecified angle of inclination relative to the horizontal plane before the sample is discharged onto the temperature-controlled sample carrier. The sample can also undergo an analysis after being discharged onto the temperature-controlled sample carrier.

One or more capture regions can be formed on a sample carrier. In this case, one or more drops of the same sample or of different samples can be discharged onto each capture region. The sample carrier must be aligned in such a way that the capture region onto which one or more drops will be placed is in the capture position. Multiple capture regions on a sample carrier allow for better utilization of the surface of the sample carrier. Advantageously, several drops are discharged onto different capture regions of the sample carrier; it is important in this case to maintain the discharge height with respect to the inclination of the sample carrier.

In order to obtain replicates and one or more negative controls, defined quantities of the same sample can be placed on a plurality of sample carriers. For this purpose, a sample carrier can also have a capture position which, although treated with all of the process fluids, does not receive a sample. This capture region can then serve as a negative control. In this way, any potential contamination of the auxiliary materials and/or the sample carrier can be detected.

In order to support a uniform wetting of the sample carrier, the same can be placed at a suitable angle of inclination with respect to the horizontal plane when the auxiliary material(s), for example the buffer, is/are applied. The applied auxiliary material(s) run(s) better in this case, and larger areas are evenly wetted by adhesion.

Before the sample is discharged onto a sample carrier, the sample carrier can be set to a prespecified, specific angle of inclination. The angle of inclination can be adjusted between 0 and 90° to the horizontal plane. In this case, the surface of the sample carrier onto which the sample will be discharged is in a horizontal plane when the angle is 0°. It lies in a vertical plane when the angle is 90°. At an angle of 90°, the sample carrier is thus vertical. The angle of inclination can be specified by the user according to the planned analysis of the sample and the type of sample. In order to prevent incorrect operation, process parameters—that is, for example, one or more of the factors: environmental conditions, quantities of auxiliary materials, quantities of media, discharge heights, discharge speeds, and angles of inclination—can also be defined by a prespecified protocol. Such a protocol can only be used by normal users after it has been compiled by specialist and competent administrators, and cannot be manipulated. This increases process reliability and prevents errors due to incorrect process parameters. The protocol typically at least defines discharge heights, discharge speeds and angles of inclination.

For discharging a sample, a defined amount of the sample is taken by the discharge device from the sample container containing a sample. The sample can be a prepared sample. To prepare the sample, the cell density of the sample can be determined, by way of example, and, if the cell density exceeds a prespecified value, can be adjusted using one or more auxiliary materials—for example, a buffer. The sample can also have been identified before the sample was taken, by an identifier (for example, a barcode) which the sample container carries. If the discharge device is a pipetting unit—for example, a pipetting robot—the prespecified amount of sample can be removed from the sample container by a pipette tip or needle. The pipette tip or needle is then aligned in such a manner that the drop is discharged from the discharge position.

The required discharge height can be shortened by increasing the discharge speed of the cell sample at the moment when it leaves the pipette tip or needle. For example, the discharge height can be set to a value in the range from 0.1 to 800 mm.

After the multiple (if applicable) discharge of one or more sample drops onto one or more sample carriers, there may be a pause of a defined length. During this time, the cell contents of the broken cell can run on the inclined sample carrier. This process can be assisted or positively influenced by a homogeneous gas flow.

To immobilize the cell components, which are now distributed on the sample carrier, fluids which are on the sample carrier, in particular auxiliary materials such as the buffer, can be evaporated. For this purpose, the temperature at the sample carrier surface can be significantly increased—for example, by a drying device—as a result of which these fluids evaporate. Alternatively, however, drying can be achieved at ambient temperature. In both cases, drying can be accelerated by a ventilated environment.

Depending on subsequent analysis methods, it may be necessary to use one or more further liquid auxiliary materials—for example, to apply a dye to the sample carrier to stain or otherwise cause a reaction of certain cell components. This approach can increase their analyzability—for example, their visibility. For the application of such fluids, either one or more further, dedicated pipette channels can be used as conveyors, or an existing pipette channel can be rinsed with an auxiliary material and used to apply the fluid auxiliary material. If necessary, a second drying can be carried out.

The samples which are positioned on the sample carrier and, if applicable, are immobilized can undergo an analysis—for example by a microscope. Used pipette tips can be discarded, used pipette needles can be cleaned—for example, by a cleaning procedure such as washing with a washing solution, by plasma, heating, or combinations thereof—and, if desired, can be sterilized before further samples are processed in the same way.

The method according to an aspect of the disclosure can be carried out in particular by the apparatus according to an aspect of the disclosure. Further features of the method according to aspect of the disclosure will become apparent from the above description of the apparatus according to an aspect of the disclosure.

The inventors have found that some environmental factors are critical to successful and traceable sample preparation. In particular, the inventors have determined the following environmental factors which have a significant influence on the results of the sample preparation:

An important factor is temperature. Low temperature of the cell sample, buffer and sample carrier promotes the bursting of the processed cells of the cell sample. The cells become more vulnerable to shear and compressive forces acting on the cells as they impact the sample carrier. This leads to an increased number of lysed cells at the same sample volume, which leads to an increased release of components of the cells of the cell sample. The components are the material of interest for a subsequent analysis. By setting a low temperature, it is possible with the same reliability of the processing results to reduce the amount of sample initially required. The greater remaining volume of the sample is then available, for example, for other procedures. Further stabilization of the sample preparation can be achieved by setting a defined, constant humidity.

A further important factor is compliance with the mixture dosage of the buffer or buffers. A buffer usually contains several components—for example, an acid component and an alcohol component. These components often tend to segregate, such that care must be taken to achieve good mixing of the buffer—or, if several buffers are used, the buffers—before the preparation. Uniform mixing of the components is easier to ensure by mechanical means than with manual preparation.

Further important factors for the success of the cell lysis and the spread of the cell components are adherence to a defined dropping height and adherence to a defined angle of inclination of the sample carrier.

A further important factor is ensuring a uniform cell count of the cell sample. The cell count must be high enough to provide sufficient, evaluable material. However, an excessively high number of cells impairs the evaluability—for example, in a subsequent microscopic examination—by spatially superimposing the analysis material, for example. By using appropriate methods for determining the cell density, it is possible to adjust the cell count of the cell samples to a uniform value, or to adjust process parameters such as drop volume, drip height, angle of inclination of the sample carrier, etc. in order to obtain comparable results.

The inventors have found that these factors significantly affect the reliability of the sample preparation. However, these factors are difficult to account for in a manual process, and can hardly be kept stable throughout the entire preparation. For this reason, the reliability of the preparation of cell samples in the laboratory and in the clinical field is usually low.

According to an aspect of the disclosure, prepared cell samples are obtained which are of high quality, and can be compared and validated. They are especially suitable for genetic analysis and/or molecular biological analyses. In addition, the disclosure makes it possible to increase the sample throughput compared to that of a manual processing. This helps to offset the increasing number of samples which are tested—concurrent with laboratory capacities which increase very slowly, leading to increased waiting times before material for analysis can be furnished.

According to an aspect of the disclosure, uniform standards for sample preparation of genetic and/or molecular biological analyses, which correspond to scientific and clinical requirements, can be achieved for the first time on the basis of defined, constant, and monitored parameters. The parameters include, in particular, one or more, and typically all of the following parameters: a controlled temperature range in the storage area, a controlled temperature range in the working area, a constant humidity in the working area, a precisely measured discharge height, a precisely measured discharge quantity, accurate observance of the inclination angle of the sample carrier, monitoring and observing the running and drying times, and environmental conditions. A further optional parameter is a precisely-regulated discharge speed.

According to an aspect of the disclosure, a cleavage of cells and the fixation of the cell components flowing out of the cells—such as chromosomes—can be achieved and high stability and reproducibility can be offered, thereby increasing the quality and significance of a subsequent—for example, optical—evaluation.

BRIEF DESCRIPTION OF THE DRAWINGS

The disclosure will now be described with reference to the drawings wherein.

DESCRIPTION OF EXEMPLARY EMBODIMENTS

Figure 1:
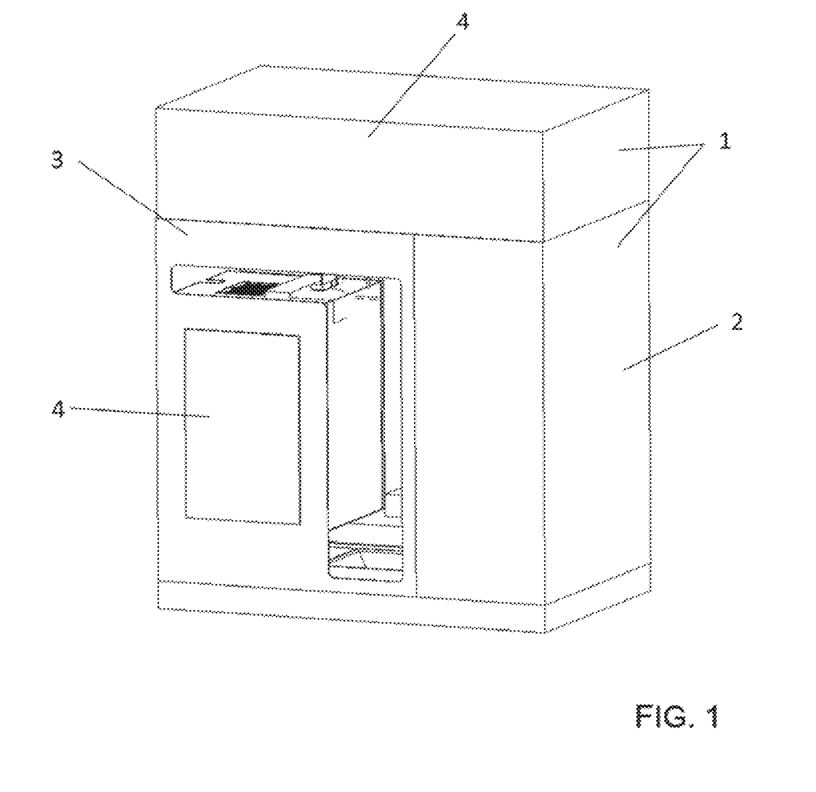
FIG. 1 shows a top view of an apparatus according to a first exemplary embodiment of the disclosure.
Figure 2:
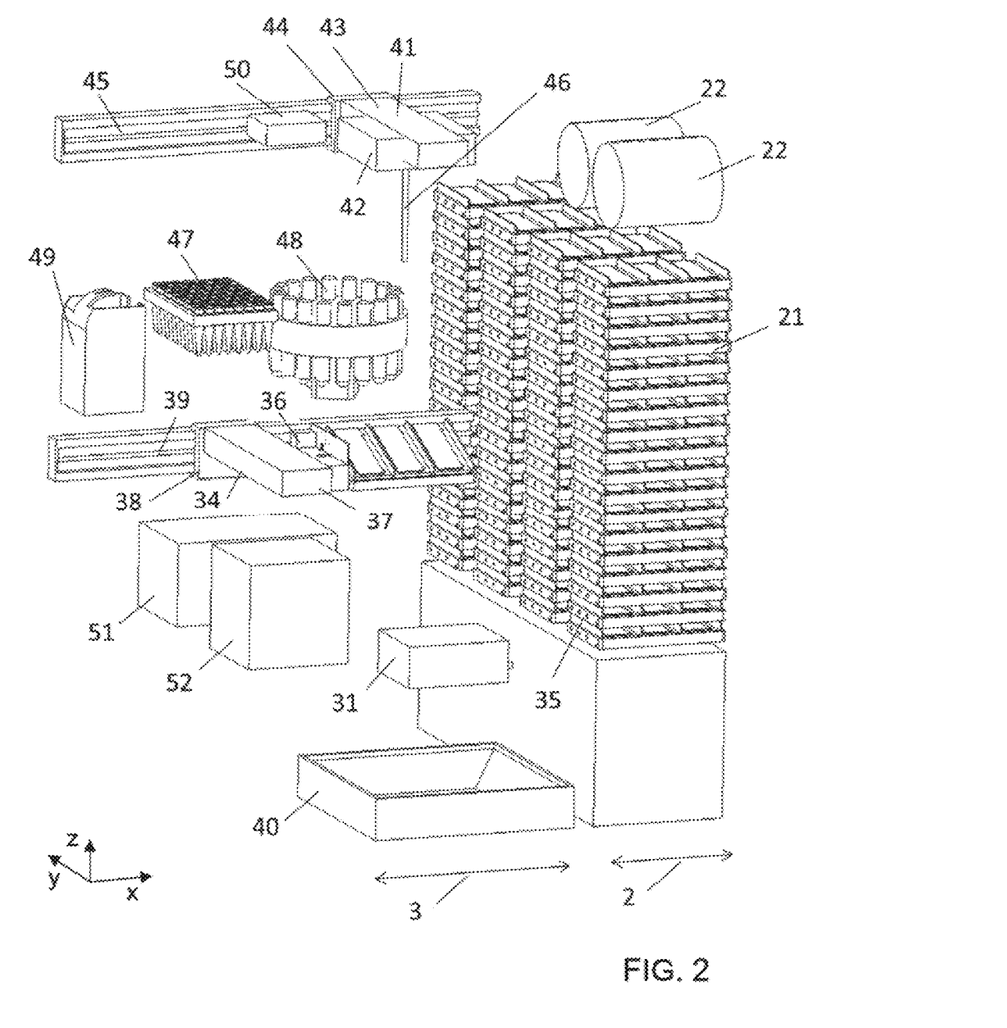
FIG. 2 shows a schematic representation of the apparatus according to the first exemplary embodiment of disclosure, without a housing.

The first exemplary embodiment of the apparatus, shown in FIGS. 1 and 2, has a housing 1. In the housing 1, a cooled storage area 2, and a working area 3 are formed as a storage area. The storage area 2 and the working area 3 are chambers within the housing 1, which are connected to each other via an opening or a lock. A climatic chamber 4 in which there are means for preparing and a conveyor configured to convey a working gas are arranged in the housing above the cooled storage area 2 and the working area 3. The working gas is the gaseous medium in the housing—for example, air. The working gas can be prepared, for example filtered, using the means for preparing the working gas. The means for preparing the working gas can be, for example, a filter. Using the conveyor configured to convey the working gas, the working gas can be conveyed from the cooled storage area 2, the working area 3, or both into the climatic chamber 4 to the means for preparing the working gas, and prepared there. Using further conveyors configured to convey the working gas, the prepared working gas can then be returned to the cooled storage area 2, the working area 3, or both. A data processing device 5—for example, a computer—is arranged outside the housing 1, and serves to control the components of the apparatus arranged in the housing. In the housing there is a sample feed 7 (see FIG. 3) which allows for the introduction of samples into the working area 3.

The cooled storage area 2 has a temperature of from −20° C. to room temperature. The working area 3 has a temperature of from −20° C.° to room temperature.

A sample carrier receiving device 21 is arranged in the cooled storage area 2, enabling the reception of a plurality of sample carriers 6. The sample carrier receiving device 21 can be a rack. Furthermore, in the cooled storage area 2, there are a first auxiliary material receiving device 22 configured to receive a first auxiliary material, and a second auxiliary material receiving device 23 configured to receive a second auxiliary material. The first auxiliary material receiving device 22 and the second auxiliary material receiving device 23 can be containers. The first auxiliary material can be a first substance needed to make a buffer. The first substance can be an alcohol. The second auxiliary material can be a second substance needed to make a buffer. The second substance can be an acid. In addition, a third auxiliary material receiving device 24 (see FIG. 3) can be arranged in the cooled storage area 2 to receive a third auxiliary material. The third auxiliary material receiving device 24 can be a container. The third auxiliary material can be, for example, a dye or a reactive solution. Further auxiliary material receiving devices can be arranged in the cooled storage area 2. It should be expressly understood that it is not absolutely necessary to produce a buffer in the apparatus according to the disclosure—for example, from the first auxiliary material and the second auxiliary material. Rather, the buffer can be introduced in ready-to-use form in an auxiliary material receiving device into the cooled storage area 2.

The samples are expediently held in sample containers—for example, in test tubes. The auxiliary materials are expediently in auxiliary material containers. The sample containers, sample carriers 6 and/or the auxiliary material containers can be identified with identifiers (for example, a barcode), enabling a unique identification of each individual sample, each sample carrier and, if applicable, each individual auxiliary material. This permits the assignment and tracking of samples, sample carriers 6, and auxiliary materials. The identifiers (for example, a barcode) can be, for example, optical codes—in particular, a barcode—or RFID tags or other identifiers. The identifiers (for example, barcodes) can be applied by known methods to the sample containers, the sample carriers 6, and the auxiliary material containers. The identifiers make it possible to comprehensively document the individual method steps together with the process parameters—for example, in reports.

In the working area 3, there is a wetting device 31 configured to wet sample carriers 6. The wetting device 31 has a mixing device (not shown) for producing an auxiliary material mixture. The wetting device 31 also has nozzles 32, via which the auxiliary material mixture can be applied to the sample carrier 6. The nozzles 32 can be one or more needles, in particular one or more washable needles, or one or more pipettes, in particular one or more pipettes with replaceable tips. Conveyors 33—for example, hoses and a pump—are provided to convey the auxiliary materials from the first and second auxiliary material receiving devices 22, 23 to the mixing device. As an alternative to the pump, a pump system can be used. It should be expressly understood that it is not absolutely necessary to produce a buffer in the apparatus according to an aspect of the disclosure—for example, from the first auxiliary material and the second auxiliary material. Rather, the buffer can be introduced in ready-to-use form in an auxiliary material receiving device into the cooled storage area 2. Thus, no mixing device is required. Rather, the buffer can be conveyed via a conveyor from the auxiliary material receiving device in which the ready-to-use buffer is held to a wetting device which has no mixing device.

By the wetting device 31, an auxiliary material or a mixture of auxiliary materials can be applied to a sample carrier 6 in a defined mixing ratio. A collecting unit 40—for example, a bowl—is arranged below the wetting device 31, and receives the portion of the auxiliary material or the auxiliary material mixture that does not adhere to the sample carrier 6.

A capture device 34 is provided for removing the sample carrier 6 from the sample carrier receiving device 21. The capture device 34 has a holding unit 35 for the sample carrier 6 and an actuator 36 for inclining the sample carrier 6 located in the holding unit 35. The holding unit 35 is movable in the x-, y-, and z-directions. The holding unit 35 and the actuator 36 may be attached via an arm 37 to a runner 38 which runs on a rail 39. The runner 38 can be moved on the rail 39—for example by a servomotor—in a horizontal direction (x-coordinate). The rail 39 is mounted (not shown) in the housing 1 in such a manner that the rail 39 is movable in the vertical direction (z-coordinate), and a second horizontal direction (y-coordinate).

In addition, a pipetting unit 41 serving as a discharge device is arranged in the working area 3. The pipetting unit 41 has a pipetting head 42, which is movable in the x-, y-, and z-directions. For this purpose, the pipetting head 42 can be attached via an arm 43 to a runner 44 which runs on a rail 45. The runner 44 can be moved on the rail 45—for example, by a servomotor—in a horizontal direction (x-coordinate). The rail 45 is mounted (not shown) in the housing 1 in such a manner that the rail 45 is movable in the vertical direction (z-coordinate), and a second horizontal direction (y-coordinate). The pipetting head can hold one or more pipettes 46. The pipettes can have pipette tips or needles. The pipette tips of the pipettes 46 are exchangeable. The pipette needles of the pipettes 46 are exchangeable. The pipette needles can be washable.

In the working area 3, there is also a pipette tip holding device 47 which can receive one or more pipette tips or needles. Furthermore, a sample receiving device 48 can be arranged in the working area 3, and can receive one or more samples. The sample receiving device 48 can be temperature-controlled—typically cooled. The sample receiving device 48 can include a cell density measuring unit 49 with which it is possible to determine the cell density of the samples prior to the discharging. In addition, a collecting vessel 49 for used pipette tips or needles can be arranged in the working area 3. The collecting vessel 49 can include an ejecting mechanism to separate the pipette tips or needles from a pipette.

One or more identification devices 50 (for example, bar code readers) can be arranged in the working area 3, allowing identification of identifiers (for example, barcodes). In addition, a drying device 51—for example, a heating device—which enables drying and thus immobilization of the sample discharged onto the sample carrier can be arranged in the working area 3. In addition, an analysis device 52—for example, a microscope—can be arranged in the working area 3, which allows an analysis of the sample which has been discharged onto the sample carrier and, if applicable, dried.

Figure 3:
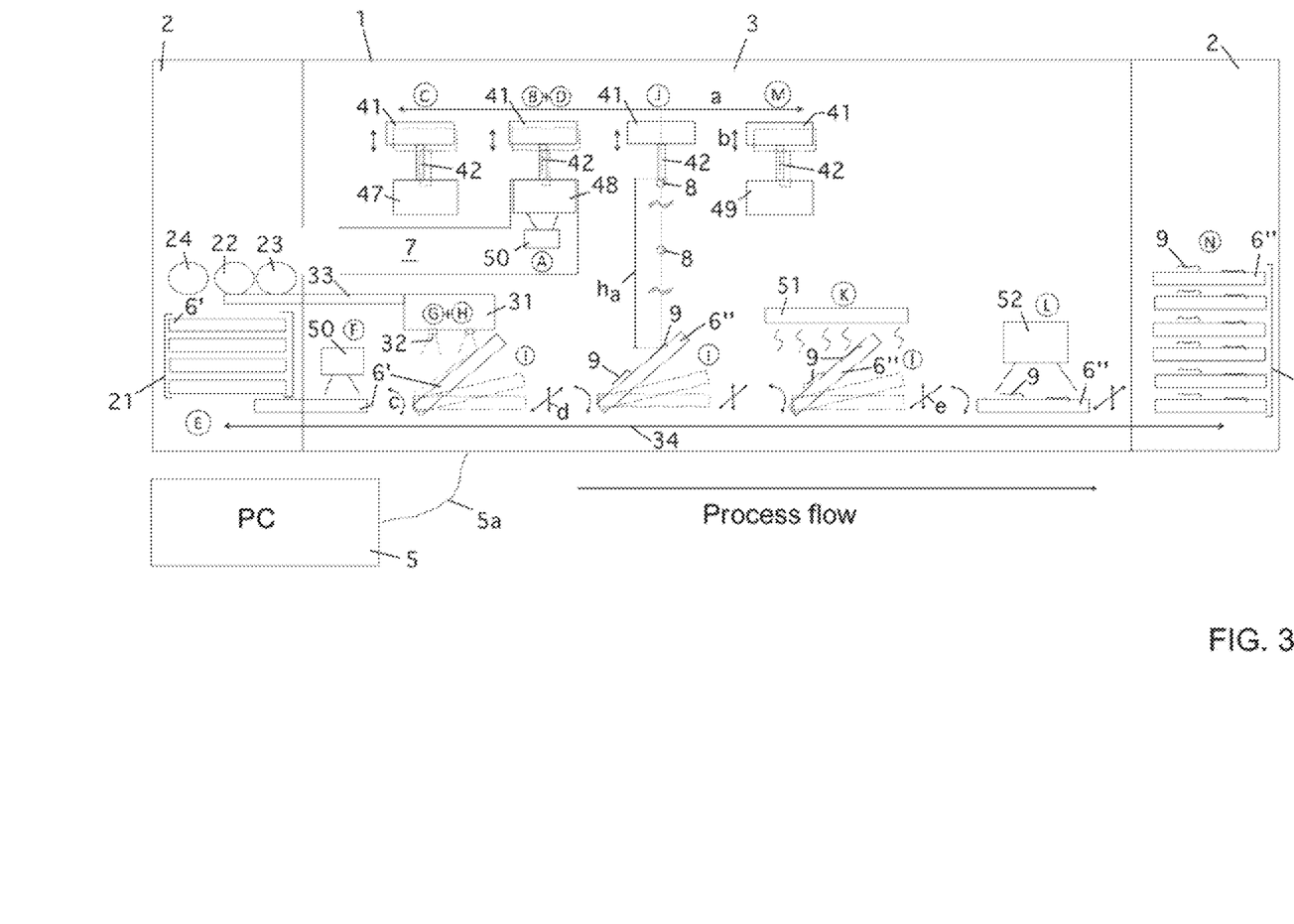
FIG. 3 shows a first flow diagram illustrating a first method sequence provided for the apparatus according to the first exemplary embodiment of the disclosure.

The method according to an aspect of the disclosure will now be explained in more detail in one exemplary embodiment with reference to FIG. 3. The flowchart shown in FIG. 3 shows the cooled storage area 2 and the working area 3. It should be noted that the cooled storage area 2 is shown twice in FIG. 3, because it serves both for receiving the empty sample carriers 6' and the wetted sample carriers 6'' carrying the discharged samples. The "process flow" arrow illustrates the process flow. The individual process steps are identified in the flowchart by capital letters in a circle.

The method sequence is explained using a sample and a sample carrier 6 as an example. However, it is also possible to simultaneously handle a plurality of samples and/or a plurality of sample carriers 6, even if this is not expressly stated. In addition, several samples can be handled successively by the apparatus. For this, the processing of a previous sample does not have to be completed. The time interval between two samples can depend on the waiting time and/or drying time needed to process a sample.

In the initial state of the apparatus according to an aspect of the disclosure, empty sample carriers 6' are located in the sample carrier receiving device 21, and the auxiliary materials required for producing the buffer—in particular, the first and second auxiliary materials—are located in the first and second auxiliary material receiving devices 22, 23, respectively. In addition, pipette tips or needles are in the pipette tip holding device 47. The auxiliary materials may be the follow auxiliary materials:

First auxiliary material: alcohol solution as the first buffer component.

Second auxiliary material: acid solution as a second buffer component.

Third auxiliary material: dye.

Fourth auxiliary material: reactive solution.

Fifth auxiliary material: washing solution.

Further auxiliary materials—for example, further dyes, reactive solutions and/or washing solutions—can be included.

The empty sample carriers 6' are uniquely identified by identifiers (for example, a barcode). The containers in which the auxiliary materials are located are clearly identified by identifiers (for example, a barcode). The cooled storage area 2 is cooled to a temperature of from −20° C. to room temperature. In the working area, a defined climate is set, namely from −20° C. to room temperature.

All settings of the apparatus, as well as the method processes—in particular, the process parameters and sample information—can be logged.

In FIG. 3, the capture device 34 is shown with a double arrow to illustrate the movement of the capture device 34 in a horizontal direction. The double arrows d and e illustrate the movement of the capture device 34 in a vertical direction and a further horizontal direction. The capture device 34 is thus movable in the x-, y-, and z-directions. The movement of the pipetting unit 41 in a horizontal direction is shown by double arrow a. The movement of the pipetting unit 41 in the vertical direction is shown by double arrow b. The pipetting head 42 is movable in the x-, y- and z-directions.

The method starts when the sample carrier receiving device 21 filled with clean sample carriers and one or more samples positioned in sample containers are introduced into the apparatus via the sample feed 7 in the housing 1, into the sample receiving device 48 and into the working area 3. The samples may have previously been pre-processed—for example, centrifuged. They can also have been previously cooled to a temperature below room temperature. The sample and/or the samples are located in sample containers which are uniquely identified by identifiers (for example, a barcode). The sample containers can be opened or closed. The sample containers can be positioned in a rack which is introduced into the working area 3 via the sample feed 7. Several racks can be introduced simultaneously into the working area 3. The samples can be further cooled after introduction into the sample receiving device 48—at least as long as they are in the sample containers.

Step A: The sample and/or the samples introduced into the sample receiving device 48 are identified by an identification device 50 (for example, a bar code reader). This is intended to allow a later assignment of the sample to a sample carrier 6.

Step B: This step is optional. For each sample located in the sample receiving device 48, the cell density of the sample is determined by the cell density measuring device. The cell density of the sample can be adjusted if the measured cell density falls below or exceeds a prespecified value. This process can be referred to as "revising the cell density." The cell density can be determined, for example, by an optical sensor and adjusted by the pipetting system and the buffer. The sample can be stained with a dye and/or mixed with a reactive solution. The dye and the reactive solution can be stored as auxiliary materials in auxiliary material receiving devices in the cooled storage area 2.

Step C: The pipetting unit 41 is conveyed to the pipette tip holding device 47 where it receives one or more pipette tips or needles. The pipette tips or needles are used to take up samples later.

Step D: The pipetting unit 41 is conveyed to the sample receiving device 48. A defined amount of a sample is taken from a sample container by a pipette 46 of the pipetting unit 41. The sample enters the pipette tip or needle of the pipette 46.

Step E: The capture device is moved into the cooled storage area 2. By the capture device 34, a sample carrier 6' is removed from the sample carrier receiving device 21, and the sample carrier 6' is moved into the holding unit 35. The sample carrier 6' is then conveyed by the capture device 34 to the wetting device 31. In the process, it passes from the cooled storage area 2 into the working area 3.

Step F: The sample carrier 6' is conveyed by the capture device to a second identification device 50 (for example, a barcode reader), and identified there. The purpose of this is to allow a later assignment of the sample to the sample carrier 6.

Step G: The first and second auxiliary materials are mixed to form an auxiliary material mixture. The auxiliary material mixture is the buffer. For the preparation of the auxiliary material mixture, defined amounts of the first and second auxiliary materials from the first and second auxiliary material receiving device 22, 23 are conveyed via the conveyor 33 to the wetting device 31 and mixed there to form a buffer. The defined amounts of the first and second auxiliary materials can correspond to a prespecified mixing ratio. If step B is included in the method, the cell density of the sample can be taken into account when the defined amount is specified. It should be noted that step G is only required if no prefabricated buffer is used. In this case, the buffer is conveyed from an auxiliary material receiving device in which it is stored and cooled, via the conveyor 33, to the wetting device 31, where it can be used directly. It should also be noted that alternatively, the auxiliary material mixture can be prepared and the samples can be wetted with drops of the auxiliary material mixture by the pipetting system. This eliminates the wetting device 31, a mixing device, or both.

Step H: The buffer is applied to the sample carrier 6' via the nozzles 32. In this case, the sample carrier 6' is rinsed with the buffer, and particularly wets the surface of the sample carrier 6' with the buffer. Several sample carriers 6' can be rinsed simultaneously. The sample carriers 6' can also be rinsed one after the other.

Step I: According to the specifications of the user of the apparatus, and optionally taking into account the results of the cell density measurement, the following parameters are now set: the discharge height, the angle of inclination of the wetted sample carrier 6', and optionally the discharge speed. To set the discharge height, the capture device 34 and the pipetting unit 41—with the pipetting head 42 which holds the pipette with the pipette tip—are aligned relative to each other. In this case, a prespecified capture region of the wetted sample carrier 6' moves into the capture position, and the pipette tip moves into the discharge position. The discharge height ha is typically set to a value in a range from 0.1 to 800 mm; the angle of inclination (double arrow c) of the wetted sample carrier 6' is set to a value in a range from 0° to 90°; and the discharge speed is set to a value in the range from 0 to 10 m/s.

Step J: A prespecified amount of the sample is discharged in one or more drops 8 from the discharge position to the prespecified capture region of the sample carrier 6', to achieve bursting of the cell nuclei of the cells contained in the sample. The prespecified amount of the sample can be discharged onto a cooled capture region of the sample carrier 6'. The sample carrier now carries at least one burst sample 9 and is therefore hereinafter referred to as the sample carrier 6". After the discharge, a waiting time can be included in the method to achieve running of the cell components of the broken cells on the sample carrier, wherein the sample carrier 6" can maintain its angle of inclination. The sample carrier 6" may optionally be transferred to a parked position.

Step K: The sample carrier 6" is conveyed in a first variant by the capture device 34 to the drying device 51. There, the surface of the sample carrier 6" or the sample carrier 6" which carries the wetted and burst sample 9 is heated as a whole to achieve evaporation of the buffer, and thus immobilization of the burst sample on the sample carrier 6". The angle of inclination of the sample carrier 6" can be set to a value in the range from 0° to 89°—that is, the angle of inclination can remain unchanged if it is not 90°. The heating can be done in a defined manner. This may involve specifying a drying temperature and specifying a drying duration. In a second variant, evaporation of the buffer and thus immobilization of the burst sample on the sample carrier 6" can be achieved by a long waiting time in a defined climate in the working area. Optionally, the drying can be supported by a blower and/or a flow of the working gas from the climatic chamber 4, already flowing in the housing 1.

Step L: This step is optional. The sample carrier 6" with the immobilized, burst sample is now conveyed by the capture device 34 to the analysis device 52. The analysis device 52 can be, for example, a microscope. The angle of inclination of the sample carrier 6" can be changed—for example, to an inclination angle of 0°, in which the surface of the sample carrier 6" carrying the fragmented sample 9 lies in a horizontal plane. There, an automated—for example, microscopic—analysis of the immobilized burst sample 9 can be carried out. In this case, the sample carrier 6" can be in a parked position.

Step M: The pipetting head 41 with the pipette 42 which carries the pipette tip used for taking up and discharging the sample is conveyed to the collecting container 49. There, the pipette tip including the non-discharged portion of the sample is discarded. If a needle has been used instead of a pipette tip, the needle is either washed, sterilized and reused in the apparatus, or is discarded. In the latter variant, the needle can be washed externally and then sterilized.

Step N: The sample carrier 6" with the immobilized, burst sample is now moved back into the cooled storage area 2 by the capture device 34. There, the sample carrier 6" can be stored in the sample carrier receiving device 21.

Figure 4:
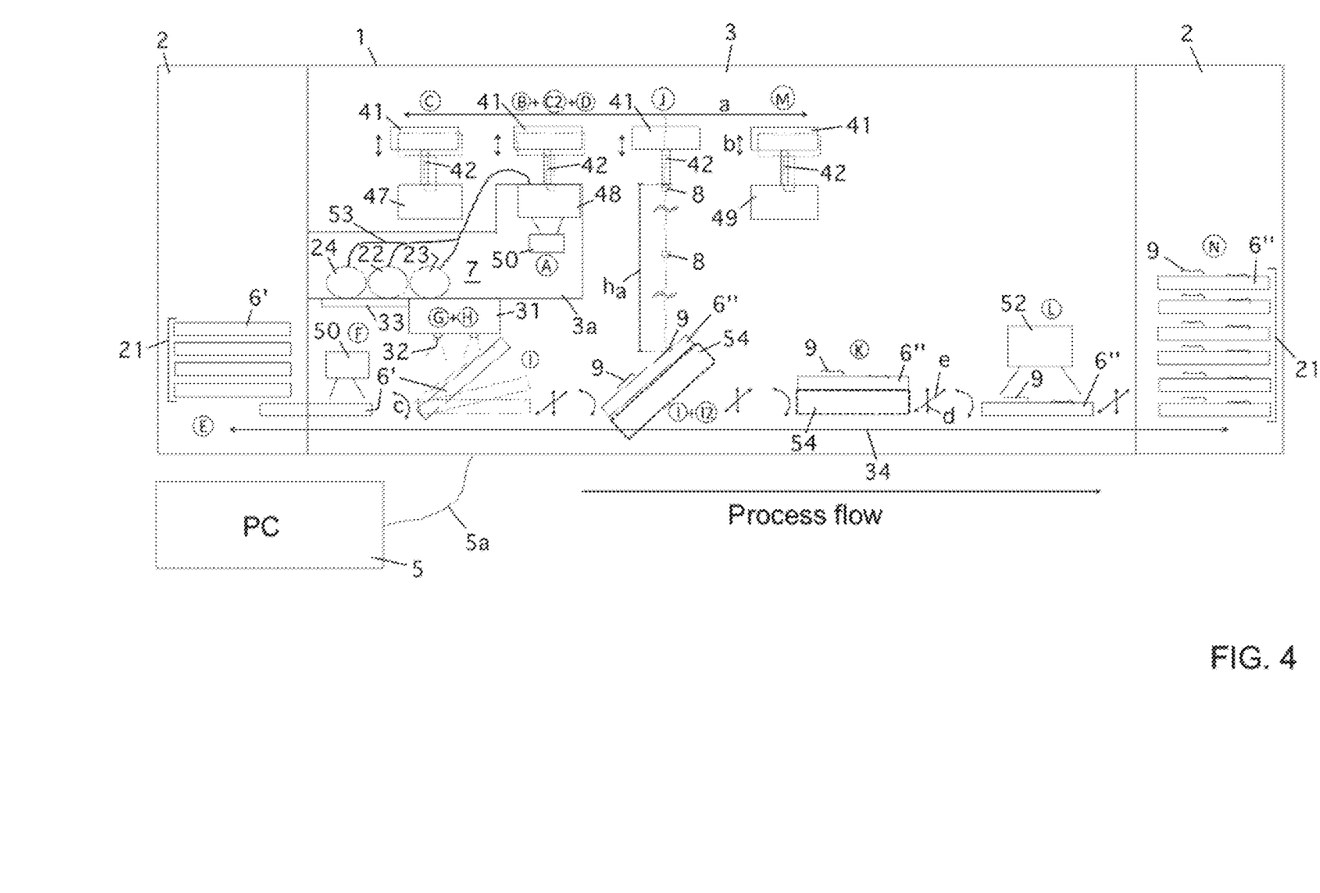
FIG. 4 shows a second flowchart illustrating a second method sequence provided for the apparatus according to the second exemplary embodiment of the disclosure.

The flowchart shown in FIG. 4 illustrates a second method sequence using a second exemplary embodiment of the apparatus according to the disclosure. The second exemplary embodiment corresponds to the first embodiment except in the following points:

(i) The storage area 2 is not a cooled storage area. The storage area 2 is instead at ambient temperature—that is, room temperature. Rather, for controlling the temperature of the sample carrier, there is a heating/cooling plate 54 as the temperature control device, on which the sample carrier 6' can be placed. The temperature control device can be part of the capture device, or formed separately. For example, the holder for receiving the sample carrier, which is also part of the capture device, can be configured in such a manner that it holds the sample carrier 6' on the heating/cooling plate 54. The actuator of the capture device can then tilt the sample carrier 6' into the prespecified angle of inclination with the heating/cooling plate 54. In a separate configuration of the temperature control device, the temperature control device can have an actuator for adjusting the angle of inclination of the sample carrier 6' deposited on it, and the temperature control device can be arranged in the apparatus in such a manner that the sample carrier 6' deposited on it is in the capture position. In this case, the capture device does not need its own actuator.

(ii) A cooled working area sub-region is constructed in the working area 3. The cooled working area sub-region 3a has a temperature of from −20° C. to room temperature; the remainder of the working area 3 has a different temperature, from −20° C. to room temperature.

(iii) The auxiliary material receiving devices 22, 23 and 24 are arranged in the cooled working area sub-region 3a.

(iv) Supply means are provided for conveying auxiliary materials from the auxiliary material receiving devices 22, 23 and 24 into the wetting means 31.

(v) The pipette tip holding device 47 holds two types of exchangeable tips or washable needles. In one exemplary embodiment, the first type of tips or needles has an uptake volume of 200 µl, and the second type of tips or needles has an uptake volume of 1000 µl. The first type is needed for mixing the sample with the auxiliary material in the sample container, which is added to adjust the given cell density. The second type is needed to extract a defined amount of the sample from the sample container.

(vi) No drying device is included.

The flowchart shown in FIG. 4 shows the storage area 2 and the working area 3, which are not temperature-controlled. It should be noted that the non-temperature-controlled storage area 2 is shown twice in FIG. 4, because it serves both for receiving the empty sample carriers 6' and the wetted sample carriers 6" carrying the discharged samples. The "process flow" arrow illustrates the process flow. The individual process steps are identified in the flowchart by capital letters in a circle.

The method sequence is explained using a sample and a sample carrier 6 as an example. However, it is also possible to simultaneously handle a plurality of samples and/or a plurality of sample carriers 6, even if this is not expressly stated. In addition, several samples can be handled successively by the apparatus. For this, the processing of a previous sample does not have to be completed. The time interval between two samples can depend on the waiting time and/or drying time needed to process a sample.

In the initial state of the apparatus, empty sample carriers 6' are located in the sample carrier receiving device 21, and the auxiliary materials required to produce the buffer—in particular, the first and second auxiliary materials—are located in the first and second auxiliary material receiving devices 22, 23, respectively. In addition, pipette tips or needles are in the pipette tip holding device 47. The auxiliary materials may be the follow auxiliary materials:

First auxiliary material: alcohol solution as the first buffer component.

Second auxiliary material: acid solution as a second buffer component.

Third auxiliary material: dye or reactive solution.

Further auxiliary materials—for example, one or more dyes, one or more reactive solutions, and/or one or more washing solutions—can be included.

The empty sample carriers 6' are uniquely identified by identifiers (for example, a barcode). The containers in which the auxiliary materials are located are clearly identified by identifiers (for example, a barcode). The storage area 2 is at ambient temperature. The temperature of the working area sub-region 3a is set to from −20° C. to room temperature. In the rest of the working area, a different defined climate is set—namely, between −20° C. and room temperature.

All settings of the apparatus, as well as the method processes—in particular, the process parameters and sample information—can be logged.

In FIG. 4, the capture device 34 is shown with a double arrow to illustrate the movement of the capture device 34 in a horizontal direction. The double arrows d and e illustrate the movement of the capture device 34 in a vertical direction and a further vertical direction. The capture device 34 is thus movable in the x-, y-, and z-directions. The movement of the pipetting unit 41 in a horizontal direction is shown by double arrow a. The movement of the pipetting unit 41 in the vertical direction is shown by double arrow b. The pipetting head 42 is movable in the x-, y- and z-directions.

The method starts when the sample carrier receiving device 21 filled with clean sample carriers and one or more samples positioned in sample containers are introduced into the apparatus via the sample feed 7 in the housing 1, into the sample receiving device 48 and into the working area sub-region 3a. The samples may have previously been pre-processed—for example, centrifuged. They can also have been previously cooled to a temperature below room temperature. The sample and/or the samples are located in sample containers which are uniquely identified by identifiers (for example, a barcode). The sample containers can be opened or closed. The sample containers can be positioned in a rack which is introduced into the working area sub-region 3a via the sample feed 7. Several racks can be introduced simultaneously into the working area sub-region 3a. The samples can be further cooled after introduction into the sample receiving device 48—at least as long as they are in the sample containers.

Step A: The sample and/or the samples introduced into the sample receiving device 48 are identified by an identification device 50 (for example, a bar code reader). This is intended to allow a later assignment of the sample to a sample carrier 6.

Step B: For each sample located in the sample receiving device 48, the cell density of the sample is determined by the cell density measuring device. The cell density of the sample can be adjusted if the measured cell density falls below or exceeds a prespecified value. This process can be referred to as "revising the cell density." For this purpose, one or more auxiliary materials can be conveyed in defined amounts via the supply means 53 from the first, second and/or third auxiliary material receiving device(s) to the sample container in which the sample is located. Alternatively, the auxiliary material(s) can be conveyed in defined amounts to the sample container in which the sample is situated, by the first type of tips or needles in step C2, from the first, second and/or third auxiliary material receiving device(s). The sample can be stained with a dye and/or mixed with a reactive solution. The dye and the reactive solution can be stored as auxiliary materials in auxiliary material receiving devices in the cooled working area sub-region 3a.

Steps C and C2: The pipetting unit 41 is conveyed to the pipette tip holding device 47 and receives there one or more pipette tips or needles of the first or second type. The pipette tips or needles of the first type are used to mix samples with one or more supplied auxiliary materials. The pipette tips or needles of the second type are used later for taking up samples. Three variants are possible: In the first variant, the cell density measured in step B corresponded to the prespecified value. The pipetting unit first takes a pipette tip or needle of the second type. In the second variant, the cell density measured in step B was above the prespecified value. The pipetting unit first takes a pipette tip or needle of the first type. Subsequently, by the pipetting unit or the supply means, prespecified amounts of one or more auxiliary material(s) are conveyed from the respective container of the auxiliary material receiving units 22, 23, 24 into the sample to reach a defined cell density. The supplied auxiliary materials are mixed with the sample. The pipette tip or needle of the first type is then discarded—for example, into the collecting vessel 49. Then, the pipetting unit 41 is conveyed again to the pipette tip holding device 47, where it takes a pipette tip or needle of the second type. In the third variant, the cell density measured in step B was below the prespecified value. An alarm is triggered, and can be presented to the user via the computer 5. The sample is either not processed, or is processed according to the user default in response to the alarm.

Step D: The pipetting unit 41 is conveyed to the sample receiving device 48. A defined amount of a sample is taken from a sample container by a pipette 46 of the pipetting unit 41. The sample enters the pipette tip or needle of the pipette 46.

Step E: The capture device is moved into the storage area 2. By the capture device 34, a sample carrier 6' is removed from the sample carrier receiving device 21, and the sample carrier 6' enters the holding unit 35 and comes to lie there on the heating/cooling plate 54. The sample carrier 6' is then conveyed by the capture device 34 to the wetting device 31. In the process, it moves from the storage area 2 into the working area 3.

Step F: The sample carrier 6' is conveyed by the capture device to a second identification device 50 (for example, a barcode reader), and identified there. The purpose of this is to allow a later assignment of the sample to the sample carrier 6.

Step G: The first and second auxiliary materials are mixed to form an auxiliary material mixture. The auxiliary material mixture is the buffer. For the preparation of the auxiliary material mixture, defined amounts of the first and second auxiliary materials from the first and second auxiliary material receiving device 22, 23 are conveyed via the conveyor 33 to the wetting device 31 and mixed there to form a buffer. The defined amounts of the first and second auxiliary materials can correspond to a prespecified mixing ratio. It should be noted that step G is only required if no prefabricated buffer is used. In this case, the buffer is conveyed from an auxiliary material receiving device in which it is stored and cooled, via the conveyor 33, to the wetting device 31, where it can be used directly. It should also be noted that alternatively, the auxiliary material mixture can be prepared and the samples can be wetted with drops of the auxiliary material mixture by the pipetting system. This eliminates the wetting device 31 and/or a mixing device.

Step H: The buffer is applied to the sample carrier 6' via the nozzles 32. In this case, the sample carrier 6' is rinsed with the buffer, and particularly wets the surface of the sample carrier 6' with the buffer. Several sample carriers 6' can be rinsed simultaneously. The sample carriers 6' can also be rinsed one after the other.

Steps I and I2: According to the specifications of the user of the apparatus, the following parameters are now set: the discharge height, the angle of inclination of the wetted sample carrier 6' resting on the heating/cooling plate 54, and optionally the discharge speed. To set the discharge height, the capture device 34 and the pipetting unit 41—with the pipetting head 42 which holds the pipette with the pipette tip—are aligned relative to each other. In this case, a prespecified capture region of the wetted sample carrier 6' moves into the capture position, and the pipette tip moves into the discharge position. The discharge height ha is preferably set to a value in a range from 0.1 to 800 mm; the inclination angle (double arrow c) of the wetted sample carrier 6' is set to a value in a range from 0° to 90°; and the discharge speed is set to a value in the range from 0 to 10 m/s. The sample carrier is still on the heating/cooling plate.

Step J: A prespecified amount of the sample is discharged in one or more drops 8 from the discharge position to the prespecified capture region of the sample carrier 6', to achieve bursting of the cell nuclei of the cells contained in the sample. The sample carrier now carries at least one burst sample 9 and is therefore hereinafter referred to as the sample carrier 6". The sample carrier is optionally in a cooled state during the dropwise deposition of the sample. It can either be actively cooled or positioned on a cold block, or covered with cold buffer. To cover the sample carrier with cold buffer, the sample carrier can be immersed, for example, in the buffer.

Step K: The sample carrier 6" is conveyed by the capture device 34 into a drying area. There, the angle of inclination of the sample carrier 6" is set to an angle of inclination of 0°, in which the surface of the sample carrier 6" carrying the burst sample 9 lies in a horizontal plane. Subsequently, the sample carrier 6" carrying the wetted and burst sample 9 is heated by the heating/cooling plate 54 to a prespecified temperature for a prespecified period of time in order to achieve evaporation of the buffer and thus immobilization of the burst sample on the sample carrier 6". The temperature can be 90° C., by way of example, and the duration can be approx. 3 to 4 minutes. Optionally, the drying can be supported by fans. It should be noted that the cooling/heating position of the sample carrier 6' or 6" can be realized as one position, or as separate positions. In the latter case, rather than one heating/cooling plate 54, there can be a cooling plate in a first position and a heating plate in a second position, or the opposite: a heating plate in a first position and a cooling plate in a second position.

Step L: This step is optional. The sample carrier 6" with the immobilized, burst sample is now conveyed by the capture device 34 to the analysis device 52. The analysis device 52 can be, for example, a microscope. By the analysis device 52, an automated—for example, microscopic—analysis of the immobilized burst sample 9 can be carried out. In this case, the sample carrier 6" can be in a parked position.

Step M: The pipetting head 41 with the pipette 42 which carries the pipette tip of the second type, used for taking up and discharging the sample, is conveyed to the collecting container 49. There, the pipette tip including the non-discharged portion of the sample is discarded. If a needle has been inserted instead of a pipette tip, the needle is ejected. The needle can then be washed and subsequently sterilized. If the needle is not discarded, it can optionally be washed, sterilized and reused in the apparatus.

Step N: The sample carrier 6" with the immobilized, burst sample is now moved back into the storage area 2 by the capture device 34. There, the sample carrier 6" can be stored in the sample carrier receiving device 21.

It is understood that the foregoing description is that of the exemplary embodiments of the disclosure and that various changes and modifications may be made thereto without departing from the spirit and scope of the disclosure as defined in the appended claims.

LIST OF REFERENCE NUMERALS 1 housing
2 cooled area
3 working area
3a working area sub-region
4 climatic chamber
5 computer
5a data connection
6 sample carrier
7 sample feed
8 drop of the sample
9 burst drop of the sample
21 sample carrier receiving device
22 first auxiliary material receiving device
23 second auxiliary material receiving device
24 third auxiliary material receiving device
31 wetting device
32 nozzle
33 conveying means
34 capture device
35 holding unit
36 actuator
37 arm
38 runner
39 rail
40 collecting unit
41 pipetting unit
42 pipetting head
43 arm
44 runner
45 rail
46 pipette
47 pipette tip holding device
48 sample receiving device
49 collecting vessel
50 identifying device
51 drying device
52 analysis device
53 supply means
54 heating/cooling plate

What is claimed is:

1. An apparatus for the automated processing of a sample containing biological cells, the apparatus comprising:
    a temperature-controlled storage area;
    a working area;
    a sample receiving device configured to receive the sample;
    an auxiliary material receiving device configured to receive auxiliary materials;
    a sample carrier receiving device configured to receive sample carriers;
    a discharge device configured to discharge the sample from a discharge position;
    at least one temperature control device configured to control a temperature of at least one of the sample carriers, and
    a capture device configured to capture the sample discharged from the discharge position in a capture position to obtain a prepared sample, and a distance between the discharge position and the capture position being adjusted to a prespecified height of between 0.1 to 800 mm, the capture device having a holder configured to receive at least one of the sample carriers, said holder being configured such that the at least one sample carrier is arranged in the capture position to obtain the discharged sample.

2. The apparatus according to claim 1, wherein the sample containing the biological cells is a blood sample or another cell sample.

3. The apparatus according to claim 1, further comprising a housing in which components of the apparatus are arranged, wherein in the housing, physical and/or chemical conditions are set which differ from the conditions of the environment.

4. The apparatus according to claim 1, wherein the discharge device includes a pipetting unit with a pipetting head movable at least along one axis.

5. The apparatus according to claim 1, wherein the temperature-controlled storage area includes at least one of the auxiliary material receiving device and the sample carrier receiving device arranged therein.

6. The apparatus according to claim 1, wherein the working area includes at least the discharge device and the capture device arranged therein.

7. The apparatus according to claim 1, wherein:
   the temperature controlled sample receiving device is arranged in the working area or in the storage area.

8. The apparatus according to claim 1, further comprising a wetting device configured to wet the sample carriers with at least one of the auxiliary materials.

9. The apparatus according to claim 1, further comprising an analysis unit configured to analyze the prepared sample.

10. The apparatus according to claim 1, wherein:
    the capture device has an actuator configured to adjust a prespecified angle of inclination of the at least one sample carrier, and
    the angle of inclination of the at least one sample carrier is adjustable to a value between 0 and 90° relative to a horizontal plane.

\* \* \* \* \*

UNITED STATES PATENT AND TRADEMARK OFFICE
CERTIFICATE OF CORRECTION

| | |
|---|---|
| PATENT NO. | : 10,907,129 B2 |
| APPLICATION NO. | : 16/396762 |
| DATED | : August 3, 2021 |
| INVENTOR(S) | : Matthias Opel et al. |

It is certified that error appears in the above-identified patent and that said Letters Patent is hereby corrected as shown below:

On the Title Page

Item (71) change:
(71) Applicant: ALS Automated Lab Solutions GmbH, Jena (DE)

To:
(71) Applicant: Sartorius Automated Lab Solutions GmbH, Jena (DE)

Signed and Sealed this
First Day of October, 2024

Katherine Kelly Vidal
*Director of the United States Patent and Trademark Office*